US008900840B2

(12) United States Patent
Hafez et al.

(10) Patent No.: US 8,900,840 B2
(45) Date of Patent: Dec. 2, 2014

(54) INTEGRATED SYSTEM FOR HYDROGEN AND METHANE PRODUCTION FROM INDUSTRIAL ORGANIC WASTES AND BIOMASS

(75) Inventors: Hisham Mohamed Hafez, London (CA); Mohamed Hesham El Naggar, London (CA); George F. Nakhla, Woodbridge (CA)

(73) Assignee: The University of Western Ontario, London, On, (CA)

( * ) Notice: Subject to any disclaimer, the term of this patent is extended or adjusted under 35 U.S.C. 154(b) by 449 days.

(21) Appl. No.: 13/147,010

(22) PCT Filed: Feb. 1, 2010

(86) PCT No.: PCT/CA2010/000132
§ 371 (c)(1),
(2), (4) Date: Sep. 23, 2011

(87) PCT Pub. No.: WO2010/085893
PCT Pub. Date: Aug. 5, 2010

(65) Prior Publication Data
US 2012/0009643 A1 Jan. 12, 2012

Related U.S. Application Data (60) Provisional application No. 61/202,137, filed on Jan. 30, 2009.

(51) Int. Cl.
*C12M 1/113* (2006.01)
(Continued)

(52) U.S. Cl.
CPC *C12P 3/00* (2013.01); *C12M 33/22* (2013.01); *Y02E 50/343* (2013.01); *C12M 23/58* (2013.01); *C12P 5/023* (2013.01); *C12M 29/18* (2013.01); *C12M 21/04* (2013.01)
USPC ...... 435/167; 435/168; 435/290.2; 435/290.4

(58) Field of Classification Search
CPC ...... C12M 21/04; C12M 33/22; C12M 23/58; C12M 29/18; C12P 3/00; C12P 5/023
See application file for complete search history.

(56) References Cited

FOREIGN PATENT DOCUMENTS

CN 201080006339.2 10/2012
DE 102006035213 1/2008
(Continued)

OTHER PUBLICATIONS

Chenlin Li et al. "Fermentative Hydrogen Production From Wastewater and Solid Wastes by Mixed Cultures," Critical Reviews in Environmental Science and Technology (2007) vol. 37: pp. 1-39, Taylor & Francis Group, LLC.

(Continued)

*Primary Examiner* — Nathan Bowers
*Assistant Examiner* — Gautam Prakash
(74) *Attorney, Agent, or Firm* — Hill & Schumacher; Lynn C. Schumacher (57) ABSTRACT

The present invention provides a system that has been devised to overcome the two most important limitations for sustained biological hydrogen production, namely contamination of the microbial hydrogen-producing cultures with methane-producing cultures necessitating frequent re-start-up and/or other methanogenic bacteria inactivation techniques, and the low bacterial yield of hydrogen-producers culminating in microbial washout from the system and failure. The system includes a continuously stirred bioreactor (CSTR) for biological hydrogen production, followed by a gravity settler positioned downstream of the CSTR, which combination forms a biohydrogenator. The biomass concentration in the hydrogen reactor is kept at the desired range through biomass recirculation from the bottom of the gravity settler and/or biomass wastage from the gravity settler's underflow. The gravity setter effluent is loaded with volatile fatty acids, as a result of microbiological breakdown of the influent waste constituents by hydrogen-producing bacteria, and is an excellent substrate for methane-forming bacteria in the downstream biomethanator.

20 Claims, 4 Drawing Sheets (51) Int. Cl.
  *C12M 1/107* (2006.01)
  *C12M 1/36* (2006.01)
  *C12P 3/00* (2006.01)
  *C12M 1/26* (2006.01)
  *C12M 1/00* (2006.01)
  *C12P 5/02* (2006.01)

(56) References Cited

FOREIGN PATENT DOCUMENTS

| EP | 0666319 | 8/1995 |
| EP | 1767284 | 3/2007 |
| EP | 1767284 A1 | 3/2007 |
| JP | 2002066518 | 3/2002 |

OTHER PUBLICATIONS

Hisham Hafez et al., "Biological Hydrogen Production From Corn-Syrup Waste Using a Novel System," Energies (2009) vol. 2, pp. 445-455.

Hisham Hafez et al., "An Integrated System for Hydrogen and Methane Production During Landfill Leachate Treatment," Proceedings of the International Conference on Hydrogen Production May 3-6, 2009.

Hisham Hafez et al., "Comparative Assessment of Decoupling of Biomass and Hydraulic Retention Times in Hydrogen Production Bioreactors," ScienceDirect, International Journal of Hydrogen Energy (2009) vol. 34, pp. 7603-7611.

Punjai T. Selvaraj et al., "Microbial Reduction of Sulfur Dioxide With Anaerobically Digested Municipal Sewage Biosolids as Electron Donors," Biotechnol. Prog. (1995) vol. 11, pp. 153-158.

INTEGRATED SYSTEM FOR HYDROGEN AND METHANE PRODUCTION FROM INDUSTRIAL ORGANIC WASTES AND BIOMASS

CROSS REFERENCE TO RELATED U.S. APPLICATIONS

This patent application is a National Phase application claiming the benefit of PCT/CA2010/000132 filed on Feb. 1, 2010, in English; which further claims the priority benefit from, U.S. Provisional Patent Application Ser. No. 61/202,137 filed on Jan. 30, 2009, in English, entitled INTEGRATED SYSTEM FOR HYDROGEN AND METHANE PRODUCTION DURING LANDFILL LEACHATE TREATMENT, and both of which are incorporated herein by reference in their entirety.

FIELD OF THE INVENTION

The present invention relates to a method and integrated system for hydrogen and methane production from industrial organic wastes and biomass.

BACKGROUND TO THE INVENTION

Biohydrogen production from organic waste addresses today's two most pressing problems: soaring energy demand and environmental pollution. Microorganisms are capable of producing hydrogen via either photosynthesis or preferably through fermentation (Matsunaga et al., 2000). Organic pollutants are anaerobically converted to methane in two distinct stages: acidification and methanogenesis. Acidification produces hydrogen as a by-product which in turn is used as an electron donor by many methanogens at the second stage of the process (Fang and Liu, 2002). Separation of the two stages is feasible for hydrogen collection from the first stage. The second stage is further used for treatment of the remaining acidification products, which includes mainly volatile fatty acids.

The continuously stirred tank reactor (CSTR) has been the most widely used system for continuous hydrogen production (Li and Fang, 2007). Since in a CSTR biomass solids residence time (SRT) is the same as the hydraulic retention time (HRT), its concentration in the mixed liquor is highly affected by the recommended HRT of 1-12 h which is optimal for high hydrogen production rates (Li and Fang, 2007). The maximum specific growth rate ($\mu_{max}$) for mixed culture of 0.333 h$^{-1}$ (Horiuchi et al., 2002) corresponds to an SRT$_{min}$ of 3.0 h.

However, high dilution rates result in a marked decrease in biomass content in the reactor due to severe cell washout and system failure (Wu et al., 2008). Decoupling of SRT from HRT in hydrogen bioreactors has been achieved primarily by using biofilms on several media including synthetic plastic media and treated anaerobic granular sludge (Das et al., 2008), activated carbon, expanded clay and loofah sponge (Chang et al., 2002), glass beads (Zhang et al., 2006) and membranes (Vallero et al., 2005). Problems with the development of methanogenic biofilms on the carrier media adversely impact process stability, which is critical for sustained hydrogen production. Moreover, membranes have not shown many advantages in terms of volumetric hydrogen yield and are also prone to fouling in such a reductive environment.

Therefore, it would be very advantageous to provide a method and integrated system for hydrogen and methane production from industrial organic wastes and biomass which decouples the solids residence time (SRT) from the hydraulic retention time (HRT) in order to avoid some of the aforementioned limitations.

SUMMARY OF THE INVENTION

The challenges for successful practical implementation of biological hydrogen production from industrial organic wastes and biomass are the low hydrogen yields, the low volumetric hydrogen production rates, microbial shifts and low hydrogen-producing microbial cultures yield.

The present invention provides a system that has been devised to overcome the two most important limitations for sustained biological hydrogen production, namely contamination of the microbial hydrogen-producing cultures with methane-producing cultures necessitating frequent re-start-up and/or other methanogenic bacteria inactivation techniques, and the low bacterial yield of hydrogen-producers culminating in microbial washout from the system and failure.

Extensive literature search using Compendex, Scifinder Scholar and Google Scholar has revealed that the concept of using a gravity settler for decoupling SRT from HRT has not been explored. Thus, in this innovative research, the use of a gravity settler after a hydrogen reactor for decoupling SRT from HRT through sludge recirculation has been investigated for the first time. In addition, an integrated hydrogen/methane production system is tested for the treatment of industrial wastes and biomass.

The system disclosed herein comprises a continuously stirred reactor (CSTR) for biological hydrogen production, followed by a gravity settler positioned downstream of the CSTR, the combination of which forms a biohydrogenator. The biomass concentration in the hydrogen reactor is kept at the desired range through biomass recirculation from the bottom of the gravity settler and/or biomass wastage from the gravity settler's underflow.

Thus, the present invention provides an apparatus for producing hydrogen and methane from organic waste, comprising:

a) a biohydrogenator including a completely mixed bioreactor having an input for receiving organic waste into said completely mixed bioreactor and a gravity settler located downstream of said completely mixed bioreactor and hydraulically connected with an output of said completely mixed bioreactor for receiving an output from said completely mixed bioreactor, including a feedback conduit connecting a bottom of the gravity settler to the completely mixed bioreactor for recirculating settled biomass from said gravity settler to said completely mixed bioreactor, and including an output conduit from the bottom of said gravity settler for discharging of excess biomass;

b) hydrogen producing microorganisms located in said completely mixed bioreactor;

c) a biomethanator located downstream of said gravity settler and hydraulically connected with an output of said gravity settler; and d) wherein the organic waste entering the completely mixed bioreactor is broken down microbiologically by hydrogen producing microorganisms to predominantly hydrogen gas and carbon dioxide, and a mixture of volatile fatty acids and primary alcohols, and wherein hydrogen gas and carbon dioxide are emitted from the completely mixed bioreactor, and wherein a liquid effluent containing the volatile fatty acids, primary alcohols and hydrogen producing microorganisms flow to the gravity settler and when in the gravity settler the hydrogen producing microorganisms settle to the bottom of the gravity settler and are concentrated in the gravity settler while liquid effluent containing predominantly the volatile fatty acids and the primary alcohols flow into the biomethanator wherein the volatile fatty acids and the primary alcohols are broken down microbiologically predominantly to methane gas and carbon dioxide, and wherein settled hydrogen producing microorganisms in the bottom of the gravity settler are recirculated back to the completely mixed bioreactor, and wherein the methane gas and carbon dioxide produced in the biomethanator are emitted and liquid waste containing residual organics are discharged from said biomethanator.

The present invention also provides a method for continuously producing hydrogen gas from organic waste, comprising:

a) seeding a completely mixed bioreactor with anaerobically digested sludge containing a mixture of microorganisms, the mixture of microorganisms including hydrogen producing microorganisms;

b) continuously flowing organic waste into the completely mixed bioreactor;

c) using the hydrogen producing microorganisms in the anaerobically digested sludge to continuously break down the organic waste in the completely mixed bioreactor and produce hydrogen gas, carbon dioxide gas, and a liquid effluent containing a mixture of volatile fatty acids, primary alcohols, and the mixture of microorganisms;

d) continuously emitting the hydrogen gas and carbon dioxide gas from the completely mixed bioreactor; and e) decoupling a solid retention time from a hydraulic retention time of the liquid effluent by flowing the liquid effluent containing the mixture of volatile fatty acids, the primary alcohols, and the mixture of microorganisms to a container located downstream of the completely mixed bioreactor, using gravity to settle and concentrate the hydrogen producing microorganisms to a bottom of the container and form a settled biomass at the bottom of the container and a liquid mixture above the settled biomass; and recirculating a portion of the settled biomass from the bottom of the container to the completely mixed bioreactor, and discharging a remaining portion of the settled biomass from the bottom of the container in an excess waste stream for controlling a concentration of the hydrogen producing microorganisms in the completely mixed bioreactor; and f) discharging the liquid mixture from the container.

Also provided is a method for continuously producing hydrogen gas and methane gas from organic waste, comprising:

a) seeding a completely mixed bioreactor with anaerobically digested sludge containing a mixture of microorganisms, the mixture of microorganisms including hydrogen producing microorganisms;

b) continuously flowing organic waste into the completely mixed bioreactor;

c) using the hydrogen producing microorganisms for continuously breaking down the organic waste for continuously producing hydrogen gas, carbon dioxide gas, and a liquid effluent containing a mixture of volatile fatty acids, primary alcohols, and the mixture of microorganisms;

d) continuously emitting the hydrogen gas and carbon dioxide gas from the completely mixed bioreactor; and e) decoupling a solid retention time from a hydraulic retention time of the liquid effluent by flowing the liquid effluent containing the mixture of volatile fatty acids, the primary alcohols, and the mixture of microorganisms to a container located downstream of the completely mixed bioreactor, using gravity to settle and concentrate the hydrogen producing microorganisms to a bottom of the container and form a settled biomass at the bottom of the container and a liquid mixture above the settled biomass; and recirculating a portion of the settled biomass from the bottom of the container to the completely mixed bioreactor, and discharging a remaining portion of the settled biomass from the bottom of the container in an excess waste stream for controlling a concentration of the hydrogen producing microorganisms in the completely mixed bioreactor; and f) flowing the liquid mixture from the container into a biomethanator located downstream of the container;

g) using unsettled microorganisms in the liquid mixture in the biomethanator for continuously breaking down the mixture of volatile fatty acids and the primary alcohols for producing methane gas and carbon dioxide gas; and h) continuously emitting the methane gas and carbon dioxide gas from the biomethanator and continuously discharging liquid waste containing residual organics from the biomethanator.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

Generally speaking, the embodiments described herein are directed to integrated system for hydrogen and methane production from industrial organic wastes and biomass. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, integrated system for hydrogen and methane production from industrial organic wastes and biomass is disclosed herein.

As used herein, the terms "about", and "approximately" when used in conjunction with ranges of dimensions, concentrations, temperatures or other physical or chemical properties or characteristics is meant to cover slight variations that may exist in the upper and lower limits of the ranges of properties/characteristics.

As used herein, the phrase "completely mixed bioreactor" means a mechanically or hydraulically agitated vessel including microorganisms in suspension and a growth media, typically comprised of nutrients such as organic carbon, nitrogen-containing compounds, phosphorous-containing compounds, and trace mineral solutions.

As used herein, the term "biomethanator" means any of the common designs used for the anaerobic conversion of organic wastes to methane and carbon dioxide. Biomethanators that include, but are not limited to, single or multi-stage continuously stirred tank reactors (CSTR), up-flow anaerobic sludge blanket reactor (UASB) where in the waste stream flows upwards through an anaerobic compacted bed of granular sludge, expanded bed granular sludge blanket (EGSB) in which waste flows upwards through an anaerobic expanded granular sludge, down-flow or up-flow anaerobic granular media reactors, anaerobic baffled tank reactor (ABR) and anaerobic migrating blanket reactor (AMBR).

As used herein, the phrase "hydrogen producing microorganisms" means microorganisms capable of fermenting organics under anaerobic conditions to produce hydrogen, carbon dioxide, and a variety of organic acids and alcohols.

As used herein, the phrase "organic waste" refers to wastes that include carbon and hydrogen such as, but are not limited to, alcohols, ketones aldehydes, volatile fatty acids, esters, carboxylic acids, ethers, carbohydrates, proteins, lipids, polysaccharides, monosaccharide, cellulose, and nucleic acids.

Figure 1:
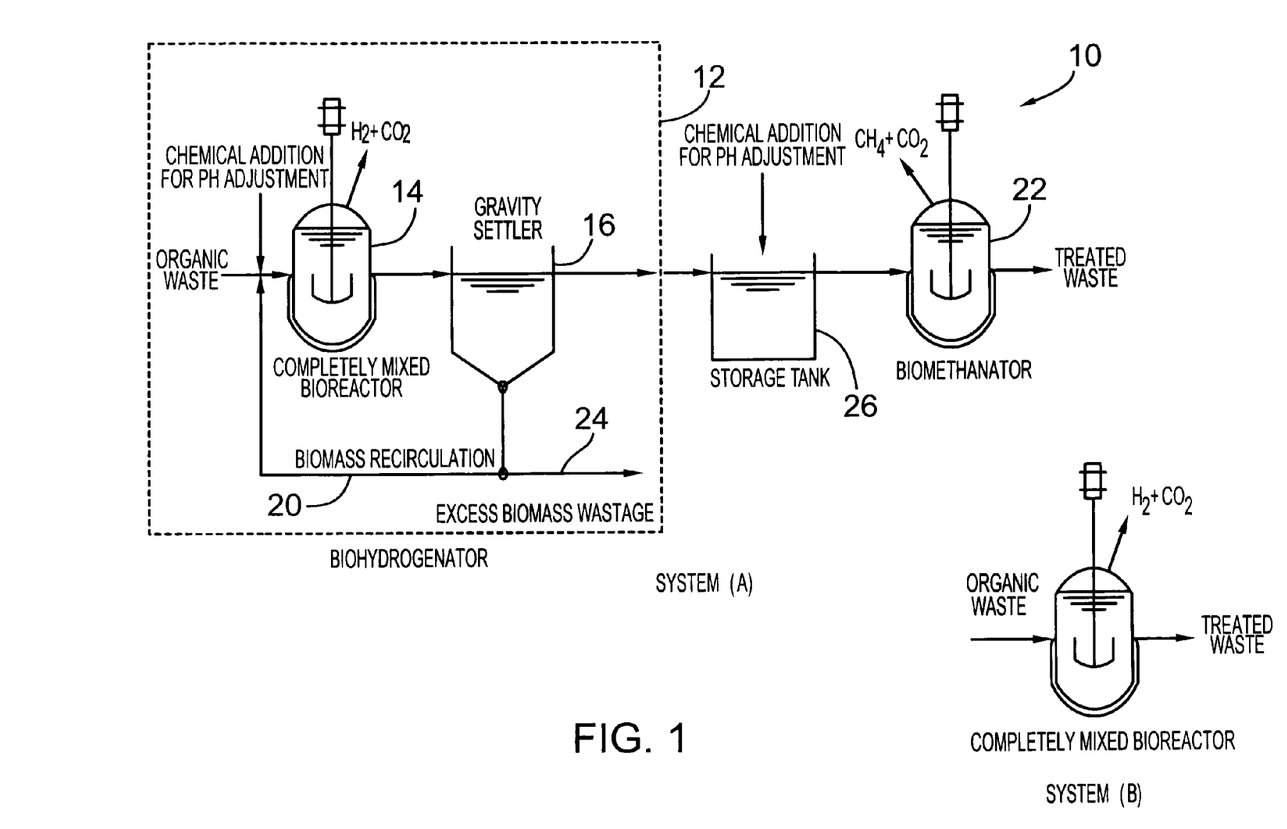
FIG. 1 is a block diagram showing the present system for employing the method of present invention.

Referring to FIG. 1, an apparatus 10 for producing hydrogen and methane from organic waste is shown. Apparatus 10 comprises a biohydrogenator 12 which includes a completely mixed bioreactor 14 (also referred to above as a continuously stirred reactor (CSTR)) having an input for receiving organic waste into the completely mixed bioreactor 14. The biohydrogenator 12 includes a gravity settler 16 is located downstream of the completely mixed bioreactor 14 and hydraulically connected with an output of the completely mixed bioreactor 14 for receiving an output from the completely mixed bioreactor 14. Apparatus 10 includes hydrogen producing microorganisms located in the completely mixed bioreactor 14 which are utilized to break down the organic waste.

Apparatus 10 includes a feedback conduit 20 connecting a bottom of the gravity settler 16 to the completely mixed bioreactor 14 for recirculating settled biomass from the gravity settler 16 to the completely mixed bioreactor 14. There is included an output conduit 24 from the bottom of the gravity settler 16 for discharging of excess biomass (excess biomass wastage in FIG. 1).

The system includes a biomethanator 22 located downstream of the gravity settler 16 and hydraulically connected with an output of the gravity settler 16. In operation, the organic waste (labelled organic waste in FIG. 1) entering the biohydrogenator 12 is broken down microbiologically by hydrogen producing microorganisms to predominantly hydrogen gas and carbon dioxide, and a mixture of volatile fatty acids and primary alcohols in the completely mixed bioreactor 14. The hydrogen gas ($H_2$) and carbon dioxide ($CO_2$) are emitted from the completely mixed bioreactor 14, and a liquid effluent containing the volatile fatty acids, primary alcohols and hydrogen producing microorganisms flow to the gravity settler 16 and when in the gravity settler 16 the hydrogen producing microorganisms settle to the bottom of the gravity settler 16 and are concentrated in the gravity settler 16. The liquid effluent containing predominantly the volatile fatty acids and the primary alcohols flow into the biomethanator 22 wherein the volatile fatty acids and the primary alcohols are broken down microbiologically predominantly to methane gas and carbon dioxide, and wherein settled hydrogen producing microorganisms in the bottom of the gravity settler 16 are recirculated back to the completely mixed bioreactor 14. The methane gas and carbon dioxide produced in the biomethanator 22 are emitted and liquid waste containing residual organics are discharged from the biomethanator 22.

The common designs for the anaerobic treatment biomethanators 22 which may be used in the present system include, but are not limited to, single or multi-stage continuously stirred tank reactors (CSTR), up-flow anaerobic sludge blanket reactor (UASB) where in the waste stream flows upwards through an anaerobic compacted bed of granular sludge, expanded bed granular sludge blanket (EGSB) in which waste flows upwards through an anaerobic expanded granular sludge, down-flow or up-flow anaerobic granular media reactors, anaerobic baffled tank reactor (ABR) and anaerobic migrating blanket reactor (AMBR).

Optionally, apparatus 10 may include a storage tank 26 hydraulically connected to the gravity settler 16 located downstream of the gravity settler 16 and which is located upstream of the biomethanator 22 and hydraulically connected to both the settler 16 and biomethanator 22 for adjusting loading rates of the liquids entering the biomethanator 22.

The apparatus may include a dispenser for dispensing chemicals into the storage tank 26 for adjusting alkalinity and pH of the liquid in the storage tank 26.

The apparatus also preferably includes temperature controllers for controlling the temperature in the completely mixed bioreactor 14 and in the biomethanator 22. A typical temperature range in which the temperature of the contents of both bioreactor 14 and biomethanator 22 is maintained is between from about 20° C. to about 70° C.

The apparatus may also include dispensing means for dispensing nutrients and pH adjustment compounds into the completely mixed bioreactor 14. The nutrients may be, but are not limited to, any one or combination of nitrogen containing compounds, phosphorous containing compounds, trace metals including iron, manganese, magnesium, calcium, cobalt, zinc, nickel, and copper. The pH adjustment compounds include, but are not limited to soda ash, sodium bicarbonate, sodium hydroxide, calcium hydroxide, magnesium hydroxide, nitric acid, and hydrochloric acid.

Examples of hydrogen generating microorganisms include, but are not limited to, *C. acetobutyricum, Bacillus thuringiensis*, and *C. butyricum*.

Examples of pH adjustment compounds include, but are not limited to soda ash, sodium bicarbonate, sodium hydroxide, calcium hydroxide, magnesium hydroxide, nitric acid, and hydrochloric acid.

System B in FIG. 1, is just the completely mixed bioreactor 14, which when connected directly to the biomethanator 22 gives the current or prior art system in use.

The present invention will now be illustrated using the following non-limiting examples.

Materials and Methods

1. Synthetic Leachate B4

Two lab-scale systems were operated at 37° C. for 25 days using systems A and B in FIG. 1 as described above. System A includes a hydrogen CSTR 14, a methane CSTR 22, intermediate gravity settler 16 and storage tank 26 to give the apparatus 10 of the present invention, as described above. System B includes a hydrogen CSTR only which is the Prior Art system. Details of the operational conditions are listed in Table 1.

Figure 6:
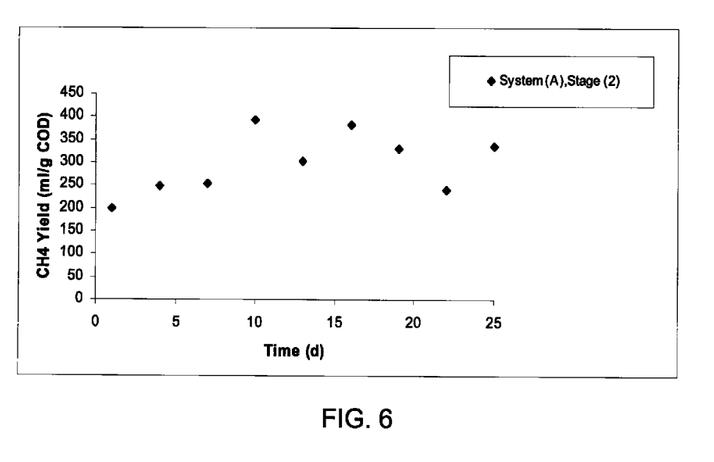
FIG. 6 shows methane yield during synthetic leachate treatment.

FIG. 6 shows that the maximum methane yield for the second stage approached the theoretical value of 393 L $CH_4$/gCOD removed. Based on extensive literature searching using Scifinder Scholar, the inventors have noted to the best of their ability that the concept of using a gravity settler for

TABLE 1

Summary of results

| Bioreactor System | HRT | SRT | R (%) | COD degradation (%) | Hydrogen Gas Content (%) | Yield (mol $H_2$/mol glucose) | Methane Gas Content (%) | Yield (ml $CH_4$/gCOD) |
|---|---|---|---|---|---|---|---|---|
| System A, Stage(1) | 8 hr | 2.2 d | 100 | 49 ± 1.8 | 43 ± 3.6 | 2.4 ± 0.3 | — | — |
| System A, Stage(2) | 10 d | 10 d | — | 77 ± 3.6 | — | — | 56 ± 8.1 | 299 ± 67.4 |
| System B Run (1) | 8 hr | 8 hr | — | 32 ± 21.8 | 25 ± 7.6 | 1.3 ± 0.8 | — | — |
| System B Run (2) | 2.2 d | 2.2 d | — | 36 ± 19 | 11 ± 6.1 | 1.1 ± 0.5 | — | — |

The experimental plan comprised two phases: phase 1 when both systems were run at an HRT of 8 h, and phase 2, when system B was switched to an HRT of 2.2 d. The systems were monitored for total COD, soluble COD, VFA, glucose, VSS, TSS and biogas composition including hydrogen, methane and nitrogen. Anaerobically-digested sludge from St. Marys wastewater treatment plant, Ontario, was used as the seed. Before startup, a portion of the sludge was preheated to 70° C. for 30 minutes to inhibit non spore forming methanogens. The feed was a synthetic leachate characterized by: 7.8 g/l of COD consisting mainly of acetic acid 3.5 ml/l; and glucose 3.5 g/l; $NaHCO_3$: 0.2 g/l; $CaCl_2$: 0.14 g/l; $MgCl_2.6H_2O$: 0.16 g/l; $NH_4HCO_3$: 0.60 g/l; $MgSO_4.7H_2O$: 0.16 g/l; urea: 1.3 g/l; $Na_2CO_3$: 0.124 g/l; $KHCO_3$: 0.156 g/l; $K_2HPO_4$: 0.015 g/l; trace mineral solution: 0.5 g/l; $H_3PO_4$: 0.44 g/l.

Results and Discussion: COD Degradation

Figure 2:
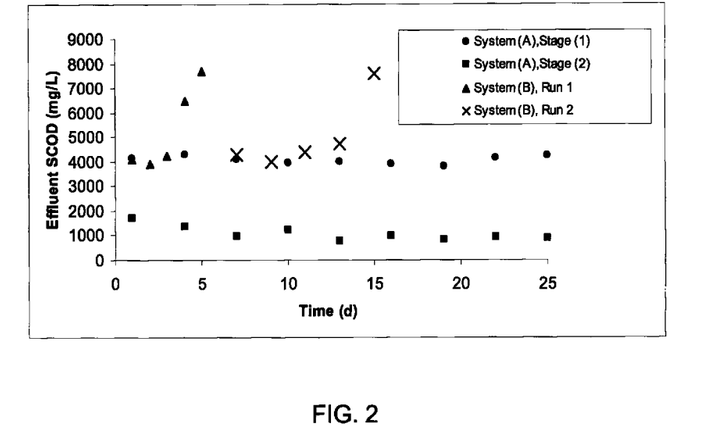
FIG. 2 shows temporal variation of effluent COD during synthetic leachate treatment using the system of FIG. 1.
Figure 3:
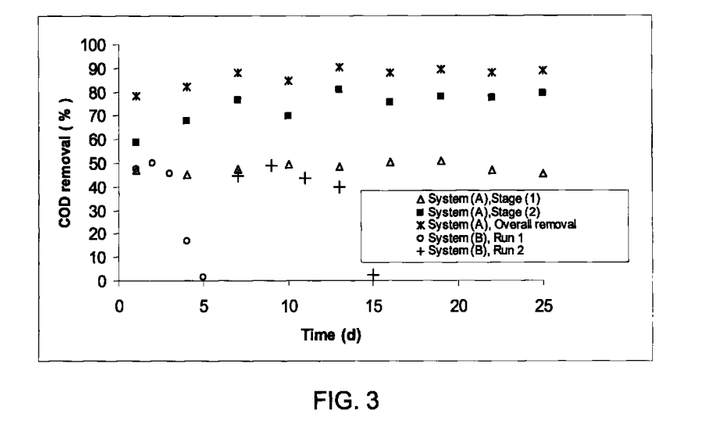
FIG. 3 shows the temporal variation of COD removal efficiency during synthetic leachate treatment.

As shown in FIG. 2, during steady state the hydrogen reactor in System A achieved complete glucose degradation, with an average effluent CODs of 4000 mg/l and 928 mg/l in stages 1 and 2, predominantly acetic acid. An overall COD removal efficiency of 88% was achieved in System A as shown in FIG. 3. FIG. 3 shows the failure of System B in COD removal efficiency after 5 days from startup at an HRT of 8 h. The biomass concentration in the hydrogen reactor at the startup was 14 gVSS/l and decreased to 0.2 gVSS/l at the end of the run due to biomass washout, with average effluent COD of 5274 mg/l and glucose degradation efficiency of only 62%. The system was subsequently restarted at an HRT of 2.2 d to mitigate biomass washout, but failed again with biomass concentration decreasing from 15 gVSS/l at startup to 0.5 gVSS/l after 9 days.

Hydrogen and Methane Production

Figure 4:
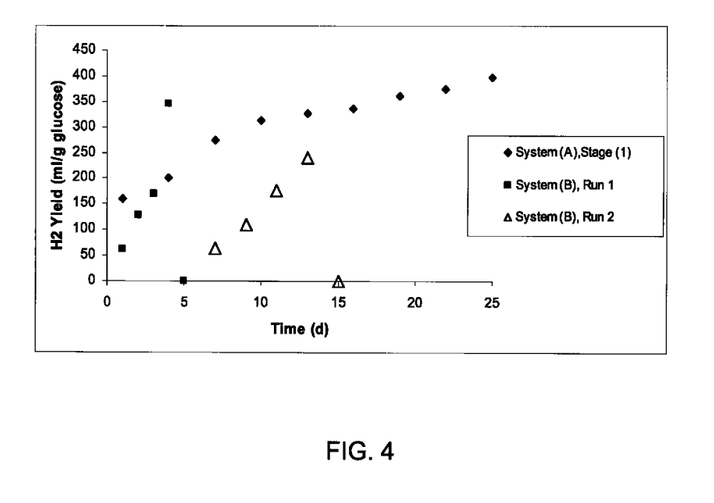
FIG. 4 shows the temporal variation of hydrogen yield during synthetic leachate treatment.
Figure 5:
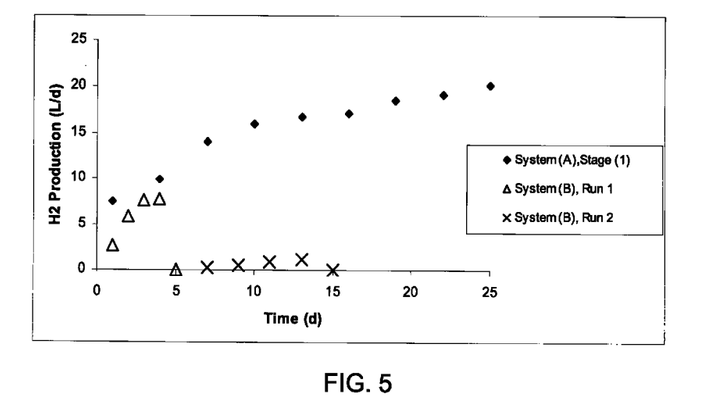
FIG. 5 shows the hydrogen production rate during synthetic leachate treatment.

Table 1 summarizes the hydrogen production for the two systems while the temporal variations are illustrated in FIGS. 4 and 5. In the new System A disclosed herein, the first reactor steadily produced hydrogen with, no methane. As depicted in FIG. 4, the maximum hydrogen yield was 397 ml $H_2$/g glucose with an average of 341 ml $H_2$/g glucose, as compared to 141 and 118 ml $H_2$/g glucose for run 1 and 2 in System B. The maximum and average hydrogen production rates in system A were 20.2 and 17.4 L $H_2$/d (FIG. 5), the maximum yield was 2.82 mol $H_2$/mol glucose higher than 1.6-2.3 mol $H_2$/mol glucose reported for continuous-flow reactors (Zhang et al., 2006).

decoupling SRT from HRT has not been disclosed. Thus, the use of a gravity settler after a hydrogen reactor for decoupling SRT from HRT through sludge recirculation is disclosed herein for the first time. In addition, an integrated hydrogen/methane production system for the treatment of industrial organic wastes and biomass is provided.

2. Real Waste

Figure 7:
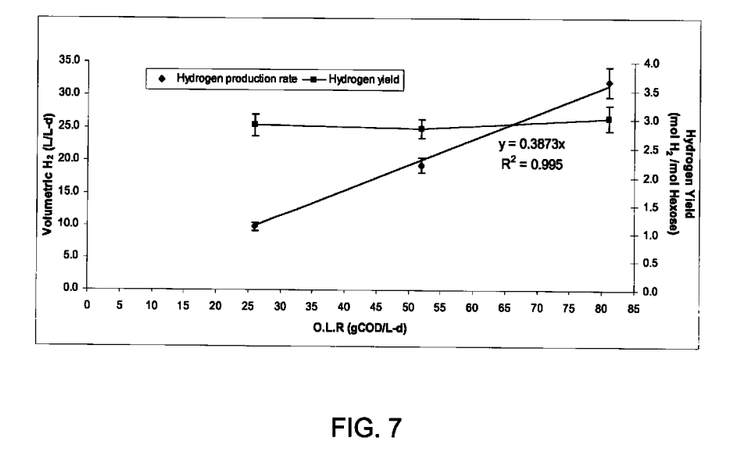
FIG. 7 shows the volumetric hydrogen production rate and molar hydrogen yield as a function of organic loading for a study involving treatment of waste including corn-syrup.

The biohydrogenator was operated for 100 days at 37° C., hydraulic retention time 8 h and solids retention time ranging from 2.2-2.5 days. The feed was a corn-syrup waste generated as a by-product from an industrial facility for bioethanol production located in South Western Ontario, Canada. The system was initially started up with a synthetic feed containing glucose at concentration of 8 g/L and other essential in-organics. Anaerobicaly-digested sludge from the St. Mary's wastewater treatment plant (St. Mary, Ontario, Canada) was used as the seed, and was heat treated at 70° C. for 30 minutes to inhibit methanogens. After 10 days, when the hydrogen production was steady, the corn-syrup waste was introduced to the system. Glucose was the main constituent in the corn-syrup; its concentration was varied over a period of 90 days from 8 to 25 g/L. The change in glucose concentration was used to study the impact of variable organic loading on the stability of hydrogen production in the biohydrogenator. As apparent from FIG. 7 the hydrogen yield was stable at 3 mol $H_2$/mol glucose while the volumetric hydrogen production rate increased from 10 L $H_2$/L/d to 34 L $H_2$/L/d with the increase of organic loading rate (OLR) from 26 to 81 gCOD/L/d. A maximum hydrogen yield of 430 mL $H_2$/gCOD was achieved in the system with an overall average of 385 mL $H_2$/gCOD.

3. Comparative Study

This study compared biological hydrogen production from glucose in two continuously stirred tank reactors (CSTR) and two biohydrogenators. The four systems were operated at organic loading rates of 6.5-42.8 gCOD/l-d, and HRTs of 8-12 hours. The SRT was maintained at 2 days in the two IBRCSs. The decoupling of SRT from HRT not only increased glucose conversion from 29-50% in the CSTR to 99.9% in the biohydrogenators, but also the volumetric hydrogen production from 0.55-1.8 in the CSTRs to 2.4-9.6 l/l-d. Biomass yields in the two biohydrogenators were 0.09 and 0.13 g VSS/g glucose converted, about 50% lower than the CSTR yields of 0.19 and 0.29 g VSS/g glucose converted. Hydrogen yield increased from 0.5-1.0 mol $H_2$/mol glucose converted in the CSTR to 2.8 mol $H_2$/mol glucose converted in the biohydrogenators. The inverse relationship between hydrogen yield and biomass yield observed in this study implies that the hydrogen yield is maximized with the minimization of biomass yield, thus necessitating decoupling of SRT from HRT to ensure sufficient reactor biomass. DGGE analysis confirmed the specificity of the microbial culture in the biohydrogenators with the presence of the high hydrogen producing *Clostridium* species, as compared to the more diverse cultures in the CSTR.

In summary, the method and apparatus disclosed herein for hydrogen and methane production from industrial organic wastes and biomass is very advantageous for several reasons. Various surprising synergistic effects were obtained as follows.

Decoupling of the sludge retention time (SRT) from the hydraulic retention time (HRT) through solids/liquid separation (using for example the gravity settler) for the hydrogen-producing bioreactor, and subsequent sludge recirculation to the hydrogen reactor, allows for operation at high biomass concentrations. The present method also surprisingly provides higher hydrogen production rates as compared with conventional completely-mixed bioreactors. The present method also provides higher hydrogen yield per mole of influent COD converted. In addition, the present method provides long-term sustainability of the system for continuous hydrogen and methane production.

The gravity settler effluent is loaded with volatile fatty acids, as a result of microbiological breakdown of the influent waste constituents by hydrogen-producing bacteria, and is an excellent substrate for methane-forming bacteria. Through the production of volatile fatty acids, the studies disclosed herein clearly show that the biohydrogenator drastically improves the efficiency of the second-stage biomethanator, increasing the volumetric methane production rate, methane yield, and solids destruction efficiency, thus allowing for higher volumetric and organic loading rates. It must be asserted that the aforementioned beneficial impact of the biohydrogenator on the second-stage anaerobic treatment process is independent of the second-stage biomethanator reactor design and/or configuration.

Finally, the present method provides a COD removal up to 90%, and energy recovery from waste and the ability to handle high organic loadings.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

Chang, J. S., Lee, K. S., and Lin, P. J., (2002) Biohydrogen production with fixed-bed bioreactors. Int. J. Hydrogen Energy 27 (11/12), 1167-1174.

Das, D., Khanna, N., Veziroglu, T. N., (2008) Recent developments in biological hydrogen production processes. Chem. Ind. And chem. Eng. 14 (2), 57-67. Horiuchi J. I., Shimizu T., Tada K., Kanno T., Kobayashi M., (2002) Selective production of organic acids in anaerobic acid reactor by pH control. Bioresource Technol 82, 209-13.

Li, C., Fang, H. H. P., (2007) Fermentative hydrogen production from wastewater and solid wastes by mixed cultures. Critical reviews in Env. Sci. and Tech., 37, 1-39.

Matsunaga, T., Hatano, T., Yamada, A., Matsumoto, M., (2000) Microaerobic hydrogen production by photosynthetic bacteria in a double phase photobioreactor. Biotechnol. Bioeng. 68 (6), 647-651.

Vallero, M. V. G., Letting a, G., and Lens, P. N. L., (2005) High rate sulfate reduction in a submerged anaerobic membrane bioreactor (SAMBaR) at high alinity. J. Membr. Sci. 253 (1/2), 217-232.

Wu, S. Y., Hung, C. H., Lin, C. Y., Lin, P. J., Lee, K. S., Lin, C. N., Chang, F. Y. And Chang, J. S. (2008) HRT-dependent hydrogen production and bacterial community structure of mixed anaerobic microflora in suspended, granular and immobilized sludge systems using glucose as the carbon substrate. Int. J. Hydrogen Energy 33, 1542-1549.

Zhang, H., Mary, A. B., Bruce, E. L., (2006) Biological hydrogen production by *Clostridium acetobutylicum* in an unsaturated flow reactor. Water Research 40, 728-734.

Therefore what is claimed is:

1. A method for continuously producing hydrogen gas from organic waste, comprising:
    a) seeding a completely mixed bioreactor with anaerobically digested sludge containing a mixture of microorganisms, the mixture of microorganisms including hydrogen producing microorganisms;
    b) continuously flowing organic waste into the completely mixed bioreactor;
    c) using the hydrogen producing microorganisms in the anaerobically digested sludge to continuously break down the organic waste in the completely mixed bioreactor and produce hydrogen gas, carbon dioxide gas, and a liquid effluent containing a mixture of volatile fatty acids, primary alcohols, and the mixture of microorganisms;
    d) continuously emitting the hydrogen gas and carbon dioxide gas from the completely mixed bioreactor; and
    e) decoupling a solid retention time from a hydraulic retention time of the liquid effluent by
        flowing the liquid effluent containing the mixture of volatile fatty acids, the primary alcohols, and the mixture of microorganisms to a container located downstream of the completely mixed bioreactor, using gravity to settle and concentrate the hydrogen producing microorganisms to a bottom of the container and form a settled biomass at the bottom of the container and a liquid mixture above the settled biomass; and
        recirculating a portion of the settled biomass from the bottom of the container to the completely mixed bioreactor, and discharging a remaining portion of the settled biomass from the bottom of the container in an excess waste stream for controlling a concentration of the hydrogen producing microorganisms in the completely mixed bioreactor; and
    f) discharging the liquid mixture from the container.

2. The method according to claim 1 including controlling a temperature of completely mixed bioreactor.

3. The method according to claim 2 wherein said temperature of the completely mixed bioreactor is maintained in a temperature range from 20° C. to about 70° C.

4. The method according to claim 1 including dispensing any one or combination of nutrients and pH adjustment compounds into the completely mixed bioreactor.

5. The method according to claim 4 wherein the nutrients are any one or combination of nitrogen containing compounds, phosphorous containing compounds, trace metals including iron, manganese, magnesium, calcium, cobalt, zinc, nickel and copper.

6. The method according to claim 4 wherein said pH adjustment compounds include, but are not limited to soda ash, sodium bicarbonate, sodium hydroxide, calcium hydroxide, magnesium hydroxide, nitric acid, and hydrochloric acid.

7. The method according to claim 1 wherein the hydrogen producing microorganisms include any one or combination of *Clostridium acetobutyricum, Bacillus thuringiensis*, and *Clostridium butyricum*.

8. The method according to claim 1, wherein the container that uses gravity to settle the hydrogen producing microorganisms is a gravity settler.

9. A method for continuously producing hydrogen gas and methane gas from organic waste, comprising:

a) seeding a completely mixed bioreactor with anaerobically digested sludge containing a mixture of microorganisms, the mixture of microorganisms including hydrogen producing microorganisms;

b) continuously flowing organic waste into the completely mixed bioreactor;

c) using the hydrogen producing microorganisms for continuously breaking down the organic waste for continuously producing hydrogen gas, carbon dioxide gas, and a liquid effluent containing a mixture of volatile fatty acids, primary alcohols, and the mixture of microorganisms;

d) continuously emitting the hydrogen gas and carbon dioxide gas from the completely mixed bioreactor; and e) decoupling a solid retention time from a hydraulic retention time of the liquid effluent by flowing the liquid effluent containing the mixture of volatile fatty acids, the primary alcohols, and the mixture of microorganisms to a container located downstream of the completely mixed bioreactor, using gravity to settle and concentrate the hydrogen producing microorganisms to a bottom of the container and form a settled biomass at the bottom of the container and a liquid mixture above the settled biomass; and recirculating a portion of the settled biomass from the bottom of the container to the completely mixed bioreactor, and discharging a remaining portion of the settled biomass from the bottom of the container in an excess waste stream for controlling a concentration of the hydrogen producing microorganisms in the completely mixed bioreactor; and f) flowing the liquid mixture from the container into a biomethanator located downstream of the container;

g) using unsettled microorganisms in the liquid mixture in the biomethanator for continuously breaking down the mixture of volatile fatty acids and the primary alcohols for producing methane gas and carbon dioxide gas; and h) continuously emitting the methane gas and carbon dioxide gas from the biomethanator and continuously discharging liquid waste containing residual organics from the biomethanator.

10. The method according to claim 9 including, prior to flowing the liquid mixture from the container into the biomethanator, first flowing the liquid mixture from the container into a storage tank located downstream of the container and which is located upstream of the biomethanator for adjusting loading rates of the liquid mixture entering the biomethanator.

11. The method according to claim 10 including dispensing pH adjustment compounds into the storage tank to adjust a pH of the contents of the contents of the storage tank.

12. The method according to claim 9 including controlling a temperature of completely mixed bioreactor and the biomethanator.

13. The method according to claim 12 wherein said temperature of completely mixed bioreactor is maintained in a temperature range from 20° C. to about 70° C.

14. The method according to claim 12 wherein said temperature of the biomethanator is maintained in a temperature range from 20° C. to about 70° C.

15. The method according to claim 9 including dispensing any one or combination of nutrients and pH adjustment compounds into the completely mixed bioreactor.

16. The method according to claim 15 wherein the nutrients are any one or combination of nitrogen containing compounds, phosphorous containing compounds, trace metals including iron, manganese, magnesium, calcium, cobalt, zinc, nickel and copper.

17. The method according to claim 15 wherein said pH adjustment compounds include, but are not limited to soda ash, sodium bicarbonate, sodium hydroxide, calcium hydroxide, magnesium hydroxide, nitric acid, and hydrochloric acid.

18. The method according to claim 9, wherein the hydrogen producing microorganisms include any one or combination of *Clostridium acetobutyricum, Bacillus thuringiensis*, and *Clostridium butyricum.*

19. The method according to claim 9, wherein the biomethanator is any one of a single continuously stirred tank reactor, a multi-stage continuously stirred tank reactor, an up-flow anaerobic sludge blanket reactor, an expanded bed granular sludge blanket, a down-flow anaerobic granular media reactor, an up-flow anaerobic granular media reactor, an anaerobic baffled tank reactor, and an anaerobic migrating blanket reactor.

20. The method according to claim 9, wherein the container that uses gravity to settle the hydrogen producing microorganisms is a gravity settler.

* * * * *